United States Patent [19]

Scopes et al.

[11] Patent Number: 4,564,618
[45] Date of Patent: Jan. 14, 1986

[54] 5-HALOVINYL-2'-DEOXYURIDINE DERIVATIVES

[75] Inventors: David I. C. Scopes, Hoddesdon; Roger F. Newton, Royston; Richard C. Cookson, Stratford Tony, all of United Kingdom

[73] Assignee: Glaxo Group Limited, England

[21] Appl. No.: 532,859

[22] Filed: Sep. 16, 1983

[30] Foreign Application Priority Data

Sep. 17, 1982 [GB] United Kingdom ................ 8226515

[51] Int. Cl.$^4$ .................. A61K 31/505; C07D 239/46
[52] U.S. Cl. .................................... 514/274; 544/309
[58] Field of Search ........................ 544/309; 424/251; 544/314

[56] References Cited

U.S. PATENT DOCUMENTS

| 4,177,348 | 12/1979 | Shealy et al. | 544/317 |
| 4,232,154 | 11/1980 | Shealy et al. | 544/250 |
| 4,396,623 | 8/1983 | Shealy et al. | 424/251 |
| 4,424,211 | 1/1984 | Jones et al. | 544/309 |

FOREIGN PATENT DOCUMENTS

| 823013222 | 9/1982 | European Pat. Off. . |
| 823039334 | 2/1983 | European Pat. Off. . |
| 823060280 | 6/1983 | European Pat. Off. . |
| 823066865 | 6/1983 | European Pat. Off. . |
| 1601020 | 10/1981 | United Kingdom . |
| 2106107 | 4/1983 | United Kingdom . |
| 2108964 | 5/1983 | United Kingdom . |

OTHER PUBLICATIONS

Shealy et al; *J. Heterocyclic Chem*; 13 (1976) pp. 1015-1020, 1041-1047, 1353-1354.
Shealy et al, *J. Med. Chem.* 1983. 26 156-161.

*Primary Examiner*—Donald G. Daus
*Assistant Examiner*—Stephen M. Kapner
*Attorney, Agent, or Firm*—Bacon & Thomas

[57] ABSTRACT

Compounds of general formula (I):

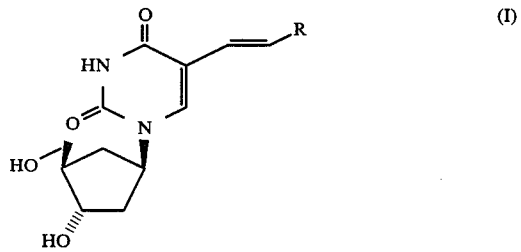

wherein R is a chlorine, bromine or iodine atom and physiologically acceptable salts thereof with bases of use as antiviral agents.

6 Claims, No Drawings

5-HALOVINYL-2'-DEOXYURIDINE DERIVATIVES

This invention relates to new uracil derivatives having antiviral activity.

Deoxyuridine derivatives such as 2'-deoxy-5-iodouridine (Prussoff and Goz: *Handbook of Experimental Pharmacology*, Part II of Antineoplastic and Immunosuppressive Agents, Springer-Verlag, New York 1975, pages 272-347) and 2'-deoxy-5-vinyluridine (Cheng et al, *Antimicrobial Agents and Chemotherapy* 10, 1, 119-122 (1976) have been found to possess antiviral activity. The activity of these compounds, however, is not very specific. British Patent Specification No. 1,601,020 discloses E-5-(2-bromo and iodo-vinyl)-2'-deoxyuridine which are described as having selective antiviral activity against herpes simplex viruses. There is a need, however, for compounds with better and more selective antiviral activity.

We have now found a small group of uracil derivatives which have improved selective activity against viruses, especially Herpetoviridae.

Thus, the invention provides compounds of the general formula (I):

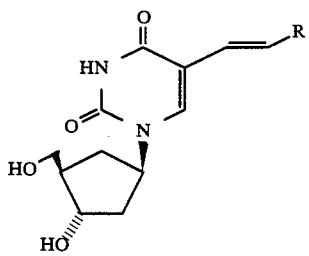

(I)

wherein R is a chlorine, bromine or iodine atom and physiologically acceptable salts thereof with bases. In particular, salts with alkali metals such as sodium and potassium may be mentioned.

In the compounds of formula (I) the halovinyl group is in the E-configuration and the pyrimidine ring is in the β-configuration relative to the cyclopentane ring.

It is to be understood that the present invention encompases the individual (+) and (−) isomeric forms of the compounds of formula (I) as well as wholly or partially racemic mixtures of such isomers. On account of their structural similarity to naturally occurring compounds such as thymidine, the 1R,3S-hydroxy-4R-hydroxymethyl-cyclopentyl isomers are of particular interest.

It will be further understood that the invention includes within its scope biological precursors of the compounds of formula (I) and their physiologically acceptable salts with bases, e.g. metabolically labile esters which are converted in vivo into the parent compound.

The compounds according to the invention may exist in tautomeric forms, for example in the form

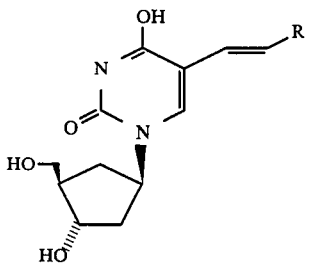

and it will be understood that such tautomeric forms are included within the scope of the invention.

Initially we found that compounds according to the invention were extremely effective substrates for thymidine kinase produced by herpes simplex virus type 1 and herpes simplex virus type 2, thus strongly suggesting that the compounds would have selective activity against strains of herpes viruses, for example, herpes simplex viruses. (J. C. Drach, *Annual Reports in Medicinal Chemistry*, 15, 1980, 149-161). Further work has indeed confirmed that these compounds are potent selective antiviral agents.

It should be noted that the compounds of formula (I) lack the glycosidic bond which forms a site for both chemical and biological cleavage in the compounds of GB-A-1,601,020. Stability against glycosidic cleavage is, of course, a valuable feature in compounds for in vivo use.

In view of their antiviral activity, the compounds of formula (I) and their physiologically acceptable salts with bases recommend themselves for the treatment of a variety of diseases caused by the Herpetoviridae, particularly herpes simplex viruses, in human beings and animals. Such diseases include stomatitis and skin eruptions, shingles, encephalitis, eye and genital herpes infections.

The invention accordingly provides compounds of formula (I) and their physiologically acceptable salts with bases for use in the therapy or prophylaxis of Herpetoviridae, e.g. herpes simplex, infections in a human or animal subject.

The compounds according to the invention may be formulated for administration in any convenient way, and the invention therefore also includes within its scope pharmaceutical compositions comprising at least one compound of formula (I) or a physiologically acceptable salt thereof with a base adapted for use in human or veterinary medicine. Such compositions may be presented for use in conventional manner in admixture with one or more physiologically acceptable carriers or excipients. The compositions may optionally further contain one or more other therapeutic agents which may if desired be a different antiviral agent.

Thus, the compounds according to the invention may be formulated for oral, buccal, parenteral, topical or rectal administration.

Tablets and capsules for oral administration may contain conventional excipients such as binding agents, for example, syrup, acacia, gelatin, sorbitol, tragacanth, mucilage of starch or polyvinyl pyrrolidone; fillers, for example, lactose, sugar, maize-starch, calcium phosphate or sorbitol; lubricants, for example, magnesium stearate, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compounds may also be formulated as suppositories, e.g. containing conventional suppository bases such as cocoa butter or other glycerides.

For buccal administration the compositions may take the form of tablets or lozenges formulated in conventional manner.

The compounds according to the invention may also be formulated for injection and may be presented in unit dose form in ampoules or in multidose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile, pyrogen-free water, before use.

For topical administration the compounds according to the invention may be formulated as ointments, creams, lotions, powders, pessaries, sprays, aerosols or drops (e.g. eye or nose drops). Ointments and creams may for example, be formulated with an aqueous or oily base with the addition of suitable thickening and/or gelling agents. Such bases may thus, for example, include water and/or an oil such as liquid paraffin or a vegetable oil such as arachis oil or castor oil. Thickening agents which may be used include soft paraffin, aluminium stearate, cetostearyl alcohol polyethylene glycols, hydrogenated lanolins and beeswax.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base, for example, talc, lactose or starch. Drops may be formulated with an aqueous or non-aqueous base also comprising one or more dispersing agents, solubilising agents or suspending agents.

Aerosol sprays are conveniently delivered from pressurised packs, with the use of a suitable propellant, e.g. dichlorodifluoromethane, trichlorofluoromethane, dichlorotetrafluoroethane, carbon dioxide or other suitable gas.

The pharmaceutical composition according to the invention may also contain other active ingredients such as antimicrobial agents, or preservatives.

The compositions may contain from 0.1%–99% of the active material. For topical administration, for example, the composition will generally contain from 0.1% to 10%, more preferably 0.5% to 5% of the active material.

For topical administration the daily dosage as employed for adult human treatment will range from 0.1 mg to 100 mg, preferably 0.5 mg to 10 mg. However, it will be appreciated that extensive skin infections may required the use of higher doses.

For systemic administration the daily dosage as employed for adult human treatment will range from 50 mg to 5 g, preferably 100 mg to 2 g, which may be administered in 1 to 4 daily doses, for example, depending on the route of administration and the condition of the patient. When the compositions comprise dosage units, each unit will preferably contain 25 mg-2 g of active ingredient, for example 50 mg to 500 mg. For serious infections the compounds may be administered by intravenous infusion using, for example 0.1 to 10 mg/kg/hr of the active ingredient.

The compounds of formula (I) according to the invention may be prepared by treatment of a compound of formula (II):

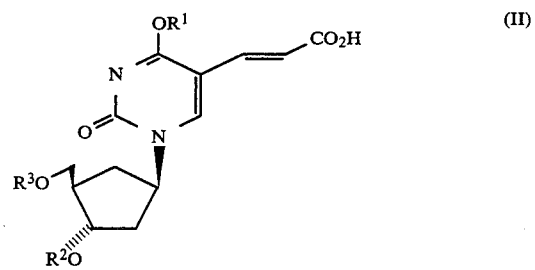

or a salt thereof (where $R^1$, $R^2$ and $R^3$, which may be the same or different, represent hydrogen atoms or protecting groups) with a halogenating agent followed where necessary by removal of any protecting groups as described hereinafter.

The reaction is conveniently effected in a medium such as water; an alcohol, e.g. methanol or ethanol; a halogenated hydrocarbon, e.g. chloroform or carbon tetrachloride; or a substituted amide, e.g. N,N-dimethylformamide, and at a temperature in the range of 0° to +100° C., preferably +30° to +70° C.

Suitable reagents for the halogenation include an N-halo amide or imide such as N-bromosuccinimide, N-chlorosuccinimide, N-iodosuccinimide, N-bromophthalimide, N-bromoacetamide, N-bromocaprolactam or 1,3-dibromo-5,5-dimethyl-hydantoin. Alternatively, molecular halogen, e.g. iodinechloride, chlorine or bromine, may be used.

In aqueous media the treatment of a compound of formula (II) with a halogenating agent is conveniently carried out in the presence of a base such as potassium acetate.

When the compound of formula (II) is used in the form of a salt the salt may be formed with an inorganic or organic base. Suitable salts include alkali metal salts, e.g. sodium or potassium salts; alkaline earth metal salts, e.g. calcium salts; or organic base salts, e.g. triethylamine or pyridine salts.

Where $R^1$, $R^2$ or $R^3$ represents a protecting group, it may be any conventional protecting group, for example, as described in 'Protective Groups in Organic Chemistry', Ed. J. F. W. McOmie (Plenum Press, 1973). Examples of suitable protecting groups are alkyl groups such as methyl, t-butyl or methoxymethyl; aralkyl groups such as benzyl, diphenylmethyl or triphenylmethyl; heterocyclic groups such as tetrahydropyranyl; acyl groups such as acetyl and silyl groups such as trialkyl silyl groups, e.g. trimethylsilyl.

The protecting groups may be removed by using conventional techniques to yield a compound of formula (I). Thus, for example, an alkyl, aryl, silyl or heterocyclic group may be removed by solvolysis, e.g. hydrolysis under acidic or basic conditions, and an aralkyl group may be cleaved with a boron trihalide e.g. boron trichloride in a solvent such as methylene chloride and at low temperature.

The compounds of formula (II) may be prepared by deprotection of the carboxyl group of a compound of formula (III):

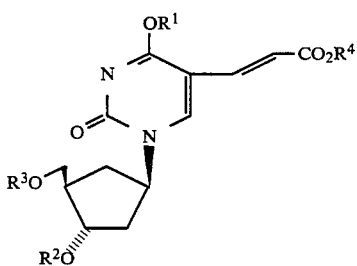
(III)

(where $R^1$, $R^2$ and $R^3$ are as previously defined and $R^4$ represents a carboxyl protecting group).

$R^4$ may be any conventional carboxyl protecting group such as an alkyl group, e.g. methyl or ethyl, or an aralkyl group, e.g. benzyl. The group $R^4$ may be cleaved by conventional means, e.g. by hydrolysis under basic conditons (using for example aqueous sodium hydroxide). The deprotection will generally be effected in the temperature range 0° to +50° C. If desired, removal of the protecting group $R^4$ may also be accompanied by removal of any protecting groups $R^1$, $R^2$ or $R^3$ where present.

The compounds of formula (III) may be prepared by reaction of a compound of formula (IV):

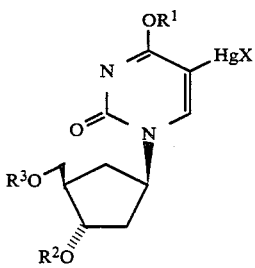
(IV)

(where $R^1$, $R^2$ and $R^3$ are as previously defined and X is an anion e.g. chloride ion) with an ester of acrylic acid:

CH$_2$=CHCO$_2$R$^4$ (where $R^4$ is as previously defined).

The reaction is conveniently carried out in the presence of a transition metal complex such as dilithium palladium tetrachloride in a solvent such as an alcohol e.g. methanol; acetonitrile; or water and at a temperature in the range of 0° to +50° C.

The compounds of formula (IV) may be prepared by reaction of a compound of formula (V):

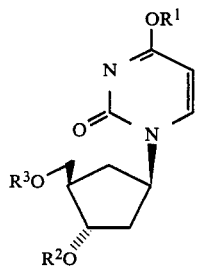
(V)

(where $R^1$, $R^2$ and $R^3$ are as previously defined) with a mercury salt HgX$_2$ (where X is as previously defined). The mercury salt may be, for example, mercuric acetate or a mercuric halide, e.g. mercuric chloride. If desired, the anion X in compounds of formula (IV) may be changed after reaction of a compound of formula (V) with a mercury salt. For example, a compound of formula (IV) in which X represents an acetate ion may be converted into a compound of formula (IV) in which X represents a chloride ion by reaction with sodium chloride.

The reaction is conveniently carried out in a solvent such as water, acetonitrile or an alcohol, e.g. methanol at a temperature in the range 0° to +100° C.

The compounds of formula (V) may be prepared by reduction of a compound of formula (VI):

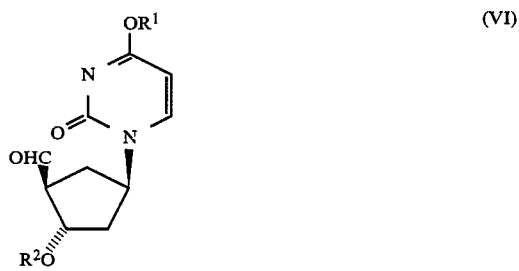
(VI)

(where $R^1$ and $R^2$ are as previous defined) followed where required by introduction of a protecting group $R^3$.

Suitable reducing agents for this reaction include alkali metal or alkaline earth metal borohydrides, such as sodium borohydride, or hydrogen in the presence of a catalyst, such as palladium on charcoal. This reaction is conveniently carried out in an organic solvent such as an alcohol, e.g. methanol or ethanol, or an ether, e.g. tetrahydrofuran, at a temperature of, for example, −20° to +80° C.

Where it is desired to introduce a protecting group $R^3$ this may be effected by conventional methods.

Where $R^2$ in the compounds of formula (V) thus produced represents a protecting group it may be convenient at this stage to remove the protecting group, for example by hydrolysis under acidic conditions using e.g. hydrochloric acid in aqueous methanol.

The compounds of formula (VI) may be prepared by hydrolysis of a compound of formula (VII):

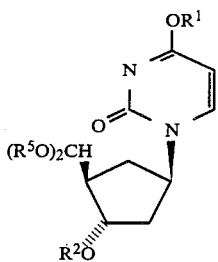

(VII)

(where $R^1$ and $R^2$ are as previously defined and $R^5$ represents a substituent derived from an alcohol or diol $R^5OH$) under acidic conditions.

The group $R^5$ may be, for example, a $C_{1-6}$ alkyl group, e.g. a methyl group, or an aralkyl group, e.g. a benzyl group. Alternatively, the acetal grouping $(R^5O)_2CH$— can be derived from a diol such that it has the structure:

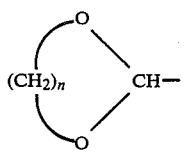

where n is, for example, 2 or 3.

Suitable acids include organic and inorganic acids such as acetic, trifluoroacetic, hydrochloric and sulphuric acids. The reaction may be effected at any temperature in the range of 0° to 100° C.

The compounds of formula (VII) may be prepared by cyclisation of a compound of formula (VIII):

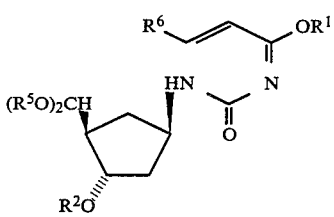

(VIII)

(where $R^1$, $R^2$ and $R^5$ are as previously defined and $R^6$ represents a leaving group). Suitable leaving groups $R^6$ include a $C_{1-6}$ alkoxy group, e.g. a methoxy or ethoxy group, a sulphonyloxy group, e.g. a methanesulphonyloxy or toluene-p-sulphonyloxy group, or a halogen atom, e.g. a chlorine or bromine atom.

The cyclisation is effected by treatment of a compound of formula (VIII) with a base such as ammonia, triethylamine, pyridine or sodium carbonate. The reaction may be carried out in any suitable solvent such as water, an alcohol, e.g. methanol, or a halogenated hydrocarbon, e.g. methylene chloride, at a temperature in the range 0° to +100° C. It will be appreciated that where $R^1$ represents hydrogen, the compounds of formula (VIII) may exist in the alternative keto form.

The compounds of formula (VIII) may be prepared by acylation of a compound of formula (IX):

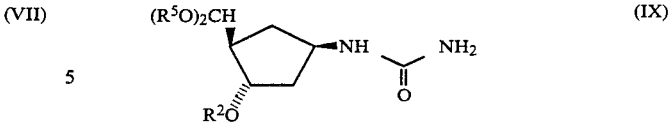

(IX)

(where $R^2$ and $R^5$ are as previously defined) with an acylating agent of formula (X):

(X)

(where $R^6$ is as previously defined and $R^7$ represents a readily displaceable atom or group). $R^7$ may be, for example, a halogen atom such as chlorine or bromine, a sulphonyloxy group such as methanesulphonyloxy or toluene-p-sulphonyloxy or an acyloxy group, i.e. such that the compound of formula (X) is a mixed anhydride formed, for example, from an alkyl haloformate such as ethylchloroformate.

The acylation may be effected in a solvent such as a ketone, e.g. acetone; a halogenated hydrocarbon, e.g. chloroform; an ester, e.g. ethyl acetate; and mixtures of such solvents, at a temperature in the range −20° to +50° C. When $R^7$ represents a halogen atom, the reaction may conveniently be carried out in the presence of an acid binding agent such as pyridine, triethylamine or sodium bicarbonate.

The compounds of formula (IX) may be prepared, for example, by a Curtius reaction. Thus, the compounds of formula (IX) may be obtained, by amination of the intermediate isocyanate generated, e.g. by conventional methods, from a compound of formula (XI):

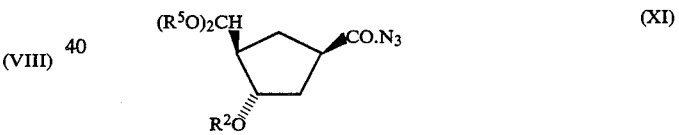

(XI)

where $R^2$ and $R^5$ are as previously defined.

The amination may be effected by using gaseous ammonia or a solution of ammonia in a solvent such as a hydrocarbon, e.g. benzene or toluene, or a halogenated hydrocarbon, e.g. chloroform.

The reaction is conveniently carried out in an organic solvent such as an ether, e.g. tetrahydrofuran; an amide, e.g. N,N-dimethylformamide; a halogenated hydrocarbon, e.g. chloroform; or a hydrocarbon, e.g. benzene and at a temperature of, for example, −20° to +50° C.

The compounds of formula (XI) may be prepared by reaction of a compound of formula (XII):

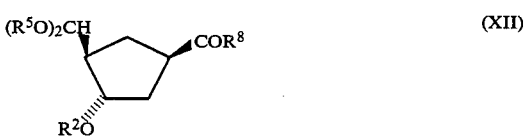

(XII)

(where $R^2$ and $R^5$ are as previously defined and $R^8$ represents a hydroxyl group or a readily displaceable atom or group) or when $R^8$ represents a hydroxyl group, a salt thereof, with a source of azide.

The readily displaceable atom or group $R^8$ may be as previously defined for $R^7$.

When $R^8$ represents an hydroxyl group the source of azide is preferably an acyl azide, for example, a phosphorus azide such as diphenylphosphoryl azide. When $R^8$ represents a readily displaceable atom or group, e.g. a chlorine atom, the source of azide may be, for example, an alkali metal or alkaline earth metal azide such as sodium azide.

The reaction is conveniently carried out in an organic solvent such as an ether, e.g. tetrahydrofuran; an amide, e.g. N,N-dimethylformamide; a halogenated hydrocarbon, e.g. chloroform; or a hydrocarbon, e.g. benzene, and at a temperature in the range of 0° to +150° C., preferably 50° to 100° C., conveniently under an atmosphere of an inert gas, such as nitrogen.

Salts of compounds of formula (XII) may be formed with inorganic or organic bases. Suitable salts include amine salts such as triethylamine, alkali metal salts, such as sodium and alkaline earth metal salts such as calcium.

The compounds of formula (XII) where $R^8$ is a readily displaceable atom or group may be prepared from the corresponding compounds where $R^8$ is a hydroxyl group by standard means.

The compounds of formula (XII) may be prepared by deprotection of a compound of formula (XIII):

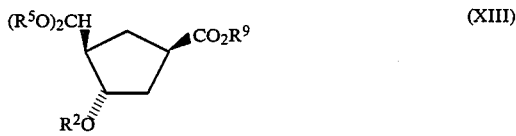

(where $R^2$ and $R^5$ are as previously defined and $R^9$ represents a protecting group).

$R^9$ may be any conventional protecting group such as an alkyl group, e.g. a methoxymethyl group, or an aralkyl group, e.g. a benzyl, diphenylmethyl or triphenylmethyl group.

The deprotection may be effected, for example, by hydrolysis, e.g. under basic conditions. Suitable bases include potassium carbonate and sodium bicarbonate.

The reaction may be carried out in an aqueous reaction medium such as water; an aqueous alcohol, e.g. aqueous methanol; or an aqueous ketone, e.g. aqueous acetone, at a temperature in the range 0° to +100° C.

The compounds of formula (XIII) may be prepared by reduction of a compound of formula (XIV):

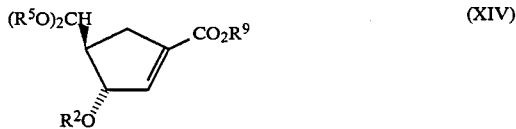

(where $R^2$, $R^5$ and $R^9$ are as previously defined).

The reduction may be carried out using hydrogen in the presence of a metal catalyst such as palladium, platinum, platinum oxide, rhodium or Raney nickel, which may be supported on, for example, charcoal, or a homogeneous catalyst such as tris triphenylphosphine rhodium chloride may be used.

The reduction may be carried out in an organic solvent such as an alcohol, e.g. ethanol; an ester, e.g. ethyl acetate or an ether, e.g. tetrahydrofuran, at a temperature in the range of 0° to 100° C.

The compounds of formula (XIV) may be prepared by treatment of a compound of formula (XV):

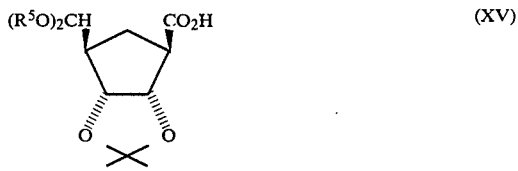

(where $R^5$ is as previously defined) or a salt thereof, with a base, followed by reaction of the intermediate thus produced with a reagent capable of introducing the protecting groups $R^2$ and $R^9$. Suitable bases for the reaction include alkyl lithium, e.g. n-butyl lithium, alkali metal hydrides, e.g. sodium hydride and lithium diisopropylamide/hexamethylphosphoramide. Suitable reagents for the introduction of the protecting groups $R^2$ and $R^9$ are, for example, alkyl and aralkyl halides such as methoxymethyl chloride and benzyl bromide.

When the compound of formula (XV) is in the form of a salt, it may be any suitable inorganic or organic base salt such as an alkali metal, e.g. sodium, alkaline earth metal, e.g. calcium, or amine, e.g. triethylamine, salt.

The reaction is conveniently carried out in an organic solvent such as an ether, e.g. tetrahydrofuran, or a hydrocarbon, e.g. benzene, at a temperature of −50° to +80° C., preferably 0° to +50° C.

The compounds of formula (XV) may be prepared by reaction of the compound of formula (XVI):

or a salt thereof with an alcohol or diol $R^5OH$ (where $R^5$ is as previously defined) or by transacetalisation.

In the reaction of the compound of formula (XVI) with $R^5OH$, the alcohol or diol will generally serve also as the reaction solvent, but a co-solvent such as a hydrocarbon, e.g. benzene or pentane, may be used if desired.

The transacetalisation may be carried out using an acetal such as 2,2-dimethoxypropane.

The source of protons in this reaction may be, for example, a mineral or organic acid such as hydrochloric, sulphuric or acetic acid, or a cationic exchange resin such as Dowex 50GX8. The reaction is conveniently carried out in the temperature range −20° to +50° C.

The compounds of formula (XVI) may be prepared by ozonolysis of a compound of formula (XVII):

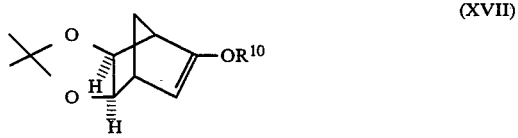

(where $R^{10}$ represents a trihydrocarbylsilyl group).

Ozonolysis is preferably effected with ozone in the presence of an organic solvent such as an alcohol, e.g. methanol, and/or a halogenated hydrocarbon e.g. dichloromethane, and at a low temperature, e.g. −100° to 0° C., conveniently at about −80° C. When the ozonolysis is completed the intermediate ozonide may be converted into a compound of formula (XVI) by the addition of a mild reducing agent such as methyl sulphide and allowing the temperature to rise.

The trihydrocarbyl silyl group $R^{10}$ may be, for example, a trialkyl, triaryl or triaralkyl silyl group, such as trimethyl silyl, t-butyl dimethyl silyl, triphenyl silyl or tribenzyl silyl.

The compounds of formula (XVII) may be prepared by the reaction of the compound of formula (XVIII):

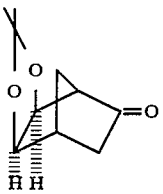
(XVIII)

with a base followed by reaction with a silylating agent.

The base may be, for example, an alkali metal hydride such as sodium hydride, an alkyl lithium such as n-butyl lithium, or lithium diisopropylamide. The silylating agent may, for example, be a trihydrocarbyl silyl halide, e.g. trihydrocarbyl silyl chloride or a trihydrocarbyl silyl sulphonate, e.g. trihydrocarbyl silyl triflate.

The reaction is preferably effected in an organic solvent such as a hydrocarbon, e.g. benzene, or an ether, e.g. tetrahydrofuran, at a temperature in the range −100° to +50° C., advantageously −80° to +20° C.

The compounds of formula (V) wherein $R^2$ and $R^3$ each represents a protecting group may alternatively be prepared by reacting compounds of formula (XIX),

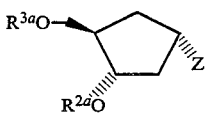
(XIX)

(where $R^{2a}$ and $R^{3a}$ represent protecting groups as previously defined in relation to $R^2$ and $R^3$ and Z represents a leaving group) with a compound of formula (XX):

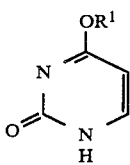
(XX)

(where $R^1$ is as previously defined) or a base salt thereof.

The reaction may be effected in an organic solvent such as for example a sulphoxide e.g. dimethylsulphoxide, an amide such as dimethylformamide, an ether e.g. tetrahydrofuran or water. The reaction is generally carried out at a temperature in the range 0° to 120° C. e.g. 30°–100° C. and in the presence of an organic or inorganic base such as sodium or potassium hydride, carbonate or bicarbonate or triethylamine. The leaving group represented by Z may, for example be a halogen atom e.g. Cl, Br or an acyloxy group such as a hydrocarbylsulphonyloxy group e.g. methanesulphonyloxy or p-toluenesulphonyloxy.

Compounds of formula (XIX) may be prepared by treatment of compounds of formula (XXI):

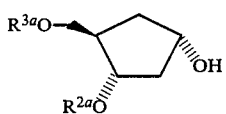
(XXI)

(where $R^{2a}$ and $R^{3a}$ are as previously defined) with a reagent serving to introduce the desired group Z. Thus, for example, a halogen atom may be introduced by halide ion displacement or using an oxyhalide reagent such as thionyl chloride. Alternatively an acyloxy group Z may be introduced by reaction with an appropriate acyl halide such as e.g. tosyl chloride. The reaction may, if desired, be carried out in the presence of a base e.g. pyridine or triethylamine and is conveniently effected in a medium such as water; an alcohol e.g. methanol or ethanol; a halogenated hydrocarbon e.g. chloroform, or carbon tetrachloride; or a substituted amide e.g. N,N-dimethylformamide, or a ketone e.g. acetone. Temperatures are generally in the range −20° C. to +70° C. e.g. 0° C. to +50° C. Alternatively, the base itself may be the solvent.

Compounds of formula (XXI) may be prepared by deprotecting compounds of formula (XXII):

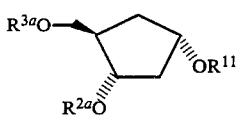
(XXII)

(where $R^{2a}$ and $R^{3a}$ are as previously defined and $R^{11}$ represents a protecting group such as those described in relation to $R^2$ and $R^3$). It will be appreciated that the group $R^{11}$ should be one which can be selectively removed, for example a trialkylsilyl group such as a dimethyltertiarybutylsilyl group. Such a group may be removed by reaction with tetraalkylammonium halides e.g. tetra-n-butylammonium fluoride or with hydrogen fluoride in aqueous acetonitrile. The reaction may conveniently be carried out in solvents such as ethers, e.g. tetrahydrofuran and at a temperature in the range −50° C. to +50° C. e.g. −20° C. to +20° C.

Compounds of formula (XXII) may be prepared by the introduction of hydroxyl protecting groups $R^{2a}$ and $R^{3a}$ into a compound of formula (XXIII):

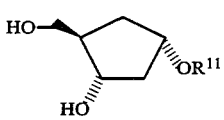
(XXIII)

(where $R^{11}$ is as previously defined).

Introduction of the hydroxyl protecting groups $R^{2a}$ and $R^{3a}$ may be carried out according to any appropriate conventional method. Suitable reagents for the introduction of protecting groups include alkyl and aralkyl halides such as methoxymethyl chloride and benzyl bromide. The reaction is optionally carried out in the presence of a base such as diisopropylethylamine and in organic solvents such as ethers e.g. tetrahydrofuran, hydrocarbons e.g. benzene, halogenated hydrocarbons e.g. dichloromethane. The reaction may be carried out in the temperature range −50° C. to +50° C. e.g. −20° C. to +20° C.

Compounds of formula (XXIII) may be prepared by ozonolysis of compounds of formula (XXIV)

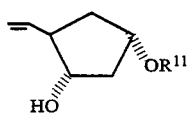
(XXIV)

(where $R^{11}$ is as previously defined) followed by the reduction of the products formed therefrom with an alkali metal borohydride such as sodium borohydride. The reaction may be carried out in organic solvents such as an alcohol e.g. methanol, halogenated hydrocarbons e.g. dichloromethane; ethers e.g. tetrahydrofuran or mixtures thereof and at a temperature in the range −70° C. to +50° C.

Compounds of formula (XXIV) may be prepared from compounds of formula (XXV):

(XXV)

(where $R^{11}$ is as previously defined) using a Grignard reagent capable of introducing a vinyl group, for example vinyl magnesium bromide. The reaction may conveniently be carried out in the presence of a catalyst such as cuprous iodide and in an organic solvent such as a halogenated hydrocarbon e.g. dichloromethane; an ether e.g. tetrahydrofuran or mixtures thereof and at a temperature in the range −70° C. to +50° C.

Compounds of formula (XXV) may be prepared from the known compound of formula (XXVI):

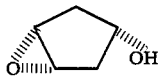
(XXVI)

by reaction with a reagent serving to introduce the protecting group $R^{11}$.

The reaction may be carried out in the presence of a coupling agent such as an imidazole and in an organic solvent such as an amide for example dimethylformamide and at a temperature in the range −50° C. to +50° C. for example −20° C. to +20° C.

According to an alternative embodiment of the invention the compounds of formula (I) may be obtained by reacting compounds of formula (XXVII):

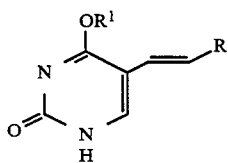
(XXVII)

(where R and $R^1$ are as previously defined) or a base salt thereof with a compound of formula (XIX) as defined above. The reaction is analogous to that described above to obtain compounds of formula (V) by reaction of compounds of formula (XIX) with compounds of formula (XX). The preferred conditions are as described for that reaction. The reaction is followed, where necessary by removal of any protecting groups as described hereinbefore.

Alternatively the compounds of formula (XIX) may be prepared in situ by treatment of a compound of formula (XXI) with a dialkylazodicarboxylate, e.g. diethylazodicarboxylate, and a tertiary phosphine e.g. triphenylphosphine in a solvent such as tetrahydrofuran or acetonitrile.

Mixtures of isomers may be separated at any convenient stage of the synthesis, for example, either before or after removal of protecting groups. Thus the desired epimer may, where necessary, be separated from the corresponding epimer by conventional means, for example, by fractional crystallisation and/or chromatography. Optically active isomers of the compounds of the invention may be obtained by resolution of the racemic mixtures using conventional means; see for example 'Stereochemistry of Carbon Compounds' by E. L. Eliel (McGraw Hill, 1962) and 'Tables of Resolving Agents' by S. H. Wilen.

The compounds of formula (I) may be converted into their salts with bases according to conventional methods by reaction with an appropriate base.

The compounds of formulae (II), (III), (IV), (VI), (VII), (VIII), (IX), (XI), (XII), (XIII), (XIV), (XV) (XVI) (XIX), (XXI), (XXII), (XXIII), (XXIV) and (XXV) are novel compounds, useful as intermediates for the preparation of compounds of formula (I), and they, together with processes for their preparation, constitute further features of the invention. Of these novel intermediates, the compounds of formulae (II), (III), (IV) and (VI) and (VII) are closely related chemically and all fall within the general formula (A):

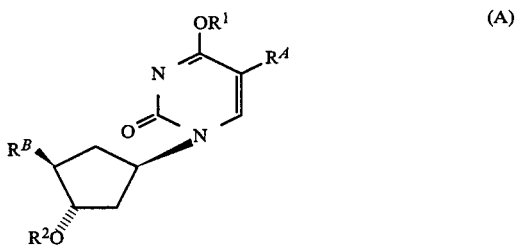
(A)

where $R^1$ and $R^2$ are as defined previously and either $R^A$ represents a group

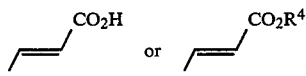

or a group HgX and $R^B$ represents a group —$CH_2OR^3$, or $R^A$ represents hydrogen and $R^B$ represents a group —CHO or —CH—$(R^5O)_2$ (in which X, $R^3$, $R^4$ and $R^5$ are as previously defined).

The compounds of formulae (VIII), (IX), (XI), (XII) and (XIII) are also closely related chemically and all fall within the general formula (B):

(B)

where R[2] and R[5] are as defined previously and R[c] represents a group of formula

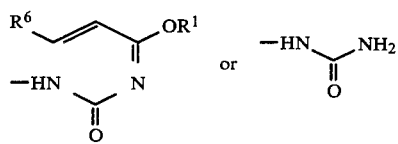

or —CON₃ or —COR[8] or —CO₂R[9] (in which R[6], R[8] and R[9] are as defined previously).

The intermediates of formulae (XIX), (XXI), (XXII), (XXIII) and (XXIV) are further closely related chemically and may be expressed as having the formula (C):

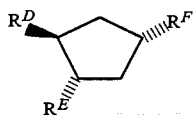

(C)

where either $R^D$ represents a hydroxymethyl group and $R^E$ represents a hydroxyl group or $R^D$ represents a protected hydroxymethyl group and $R^E$ represents a protected hydroxyl group or $R^E$ represents a hydroxyl group and $R^D$ represents an ethenyl group and $R^F$ represents a hydroxyl or protected hydroxyl group or a group Z as defined above with the proviso that either $R^D$ represents a protected hydroxymethyl group and $R^E$ represents a protected hydroxyl group or $R^F$ represents a protected hydroxyl group.

The following examples illustrate the invention. Temperatures are in °C. The nomenclature used is in accordance with the Chemical Abstracts system.

Solutions were dried by use of magnesium sulphate. Flash column chromatography was carried out over silica using the method described by W. E. Still et al, *J. Org. Chem.* 1978, 14, 2923.

INTERMEDIATE 1

(3aα, 4β, 7β,7aα)-(±)-5-[[(1,1-Dimethylethyl)dimethylsilyl]-oxy]-3a 4, 7, 7a-tetrahydro-2,2-dimethyl-4,7-methano-1,3-benzodioxole A solution of lithium diisopropylamide was prepared by treating diisopropylamine (10.5 g) in dry THF (90 ml), cooled to −15° under nitrogen, with n-butyl lithium (61.2 ml, 1.7M solution in hexane). After stirring for 10 min. at ca −10° to −20°, the solution was cooled to −70° and a solution of (3aα, 4β, 7β, 7aα)-(±)-tetrahydro-2,2-dimethyl-4,7-methano-1,3-benzodioxol-5-(4H)-one (15.8 g) in dry THF (40 ml) was added dropwise over 15 min. keeping the temperature lower than −65°. The solution was stirred at −70° for 0.75 h, hexamethylphosphoramide (13 ml) was added, followed by t-butyldimethylsilyl chloride (14.2 g) in dry pentane (11 ml). The mixture was allowed to warm up to room temperature over 2 h, poured into pentane (300 ml) and the organic phase washed with water (1×100 ml, 1×40 ml). The solution was dried and concentrated to afford crude title compound as an oil. Kugelrohr distillation give pure title compound as a yellow oil (21.6 g).

τ(CDCl₃ 5.36 (1H,d,=CH—), 5.54, 5.65 (2H, AB doublet m, H-5, H-6), 8.51, 8.61 (6H, 2xs, 2xMe).

INTERMEDIATE 2

(3aα, 4α,6aα)-(±)-6-(Dimethoxymethyl)tetrahydro-2,2-dimethyl-4aH-cyclopenta-1,3-dioxole-4-carboxylic acid Oxygenated ozone was bubbled through a solution of Intermediate 1 (20.0 g) in dry methanol (190 ml) and dry methylene chloride (60 ml) at −70° until a blue colouration appeared. Dimethyl sulphide (14 ml) was added and the reaction mixture slowly allowed to reach room temperature. The solvents were evaporated and the residue taken up in 2,2-dimethoxypropane (190 ml) and dry methanol (10 ml). After cooling to 0°, Dowex 50W-X8[H+] (9 g) was added and the reaction mixture stirred at 0° for 3 days. The resin was removed by filtration and the solvents evaporated in vacuo. The residue was purified by flash chromatography, eluting with methanol-methylene chloride (3:97), to give the title compound (10,4 g) as a solid, m.p. 82°–83.5°.

INTERMEDIATE 3

(3β, 4α)-(±)-Methoxymethyl 4-(dimethoxymethyl)-3-(methoxymethoxy)-1-cyclopentene-1-carboxylate A solution of lithium diisopropylamide was prepared by treating diisopropylamine (17.2 g) in dry THF (250 ml), cooled to −20° under nitrogen, with n-butyl lithium (99 ml, 1.7M solution in hexane). The mixture was cooled to ca. −65° and stirred for a further 0.5 h. A solution of Intermediate 2 (10.4 g) in dry THF was added dropwise over 20 min., keeping the temperature −60°. The solution was then allowed to slowly warm to room temperature and stirring continued for 1.5 h. Methoxymethyl chloride (18.44 g) was added and the reaction mixture allowed to stir at room temperature for 18 h. The THF was evaporated in vacuo and the residue was partitioned between diethyl ether (400 ml) and water (50 ml). The organic phase was washed with saturated ammonium chloride solution (30 ml), saturated sodium bicarbonate solution (50 ml) and dried. Removal of the solvent gave the title compound as an oil (11.8 g).

τ(CDCl₃) 2.25 (1H, =CH), 4.67 (2H, CO₂C$\underline{H}$₂OMe), 5.16–5.34 (3H, m,

C$\underline{H}$OC$\underline{H}$₂OMe), 5.66 (1H,d,C$\underline{H}$(OMe)₂), 6.50, 6.59 (12H, 4xs, 4xOMe); νmax (liq.film) 1720, 1640 cm⁻¹.

INTERMEDIATE 4

(3β,4α)-(±)-Methoxymethyl 3-(dimethoxymethyl)-4-(methoxymethoxy)-1-cyclopentane-carboxylate Intermediate 3 (17.6 g) and 5% palladium on charcoal (5.5 g) in ethanol (300 ml) was stirred under a hydrogen atmosphere for 4 hours and the reaction mixture was then filtered. The catalyst was washed with ethanol (300 ml) and the combined filtrate and washings were evaporated under reduced pressure to give the title compound (16 g) as a mixture of epimers. τ(CDCl₃) 4.75(2H,CO₂C$\underline{H}$₂OMe), 5.35(2H, CHOC$\underline{H}$₂OMe), 5.70–6.00(1H,m,

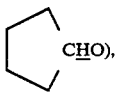

6.55, 6.60(12H, 4xS, 4xOMe); $\nu$max(CCl$_4$) 1745 cm$^{-1}$.

INTERMEDIATE 5

(3$\beta$,
4$\alpha$)-($\pm$)-3-(Dimethoxymethyl)-4-(methoxymethoxy)-1-cyclopentane-carboxylic acid Potassium carbonate (40 g) was added to a solution of Intermediate 4 (16 g) in methanol (100 ml) and water (200 ml) and the reaction mixture was stirred for approximately 16 hours. The solution was washed with methylene chloride (150 ml) and the aqueous phase was acidified with 2N HCl (320 ml) and extracted with methylene chloride (3×300 ml). The organic layer was dried and concentrated to give the title compound (8.2 g) as a mixture of epimers.

$\tau$(CDCl$_3$) 1.0–3.0(1H, br, CO$_2$H), 5.3–5.4 (2H, m, MeOCH$_2$), 5.87, 5.96 (1H, m,

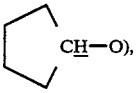

6.65 (9H, 3s, 3xOMe) 7.00, 7.18 (1H,m,CH$_2$CO$_2$H).

INTERMEDIATE 6

(3$\beta$,
4$\alpha$)-($\pm$)-N-[[[3-(Dimethoxymethyl)-4-(methoxymethoxy)cyclopentyl]amino]carbonyl]-3-ethoxy-2-propenamide To Intermediate 5 (2.8 g) and triethylamine (1.7 ml) in dry benzene (50 ml) under a nitrogen atmosphere was added diphenylphosphoryl azide (3.1 g) and the resulting solution refluxed for 1.25 hours. Ammonia gas was then bubbled through the solution at 5° to 10° for 40 minutes. The solvent was completely removed, the residue taken up in chloroform (50 ml) and pyridine (2.25 ml) added. The solution was cooled (ice bath), $\beta$-ethoxyacryloyl chloride (2.25 ml) added, and the mixture stirred at room temperature. After 48 hours, more acid chloride (2.25 ml) was added and stirring continued for a further 12 hours. Water (30 ml) was added, the aqueous layer was extracted with chloroform (30 ml) and the combined organic layers washed with 5% aqueous potassium hydrogen sulphate (30 ml, 15 ml) and aqueous sodium bicarbonate (50 ml) and dried. Evaporation of the solvent afforded an oil, which was purified by flash column chromatography eluting with 5% methanol/methylene chloride to give the title compound (2.23 g) as a mixture of epimers.

$\tau$(CDCl$_3$) 2.37(1H,d, —CH═CHOEt), 5.31(1H,d, —CH═CHOEt), $\nu$max (CCl$_4$), 1680, 1620, 1545 cm$^{-1}$.
Analysis Found: C,53.47; H 7.83; N, 7.66%. C$_{16}$H$_{28}$N$_2$O$_7$ requires C,53.32; H,7.83; N, 7.77%.

INTERMEDIATE 7

($\pm$)-1-[(3$\beta$,4$\alpha$)-3-(Dimethoxymethyl)-4-(methoxymethoxy)cyclopentyl]-2,4(1H, 3H)-pyrimidinedione Intermediate 6 (2.23 g) was refluxed in 0.88 aq. ammonia (150 ml) for 2 hours and the solvent removed below 40° under reduced pressure. The residue was partitioned between methylene chloride (50 ml) and saturated aqueous sodium bicarbonate (30 ml). The aqueous layer was extracted with methylene chloride (2×25 ml), the combined organic layers dried and the solvent removed by evaporation under reduced pressure to yield the title compound (1.57 g) as a mixture of epimers. A small portion of the product was purified by flash column chromatography eluting with 5% methanol/methylene chloride.

$\tau$(D$_2$O) 2.40, 2.67(1H,d,H-6) 4.25, 4.26 (1H,d,H-5), 4.85(1H,m,H-1').

INTERMEDIATE 8

($\pm$)-1-[(3$\beta$,4$\alpha$)-3-(Hydroxymethyl)-4-(methoxymethoxy)cyclopentyl]-2,4(1H,3H)-pyrimidinedione Intermediate 7 (2.05 g) was heated in 80% aq. acetic acid (50 ml) for 15 minutes at 80°–85°. The solution was diluted with benzene (200 ml) and the benzene removed at room temperature under reduced pressure. Toluene (200 ml, 100 ml) was twice added and removed at 25°–30° under reduced pressure. The residue was dissolved in dry methanol (25 ml) and ethanol (5 ml), and sodium borohydride (380 mg) added at 0°. The mixture was stirred for fifteen minutes at room temperature, acetone (1 ml) added, and the solvent removed under reduced pressure. The residue was dissolved in dry methanol (20 ml) and trifluoroacetic acid (ca.0.6 ml) added to acidify the solution (pH 2). Removal of the solvent under reduced pressure and purification of the product by flash column chromatography eluting with 10% methanol/methylene chloride gave the title compound (1.3 g) as a mixture of epimers.

$\tau$(CDCl$_3$) 2.43, 2.7(1H,d,H-6), 4.25, 4.26(1H,d,H-5), 4.75(1H,m,H-1').

INTERMEDIATE 9

($\pm$)-1-[(3$\beta$,4$\alpha$)-3-Hydroxy-4-(hydroxymethyl)cyclopentyl]-2,4(1H,3H)-pyrimidinedione A solution of Intermediate 8 (1.3 g) in methanol (30 ml) containing conc. hydrochloric acid (0.5 ml) was refluxed for 25 minutes. The solution was neutralised with 2N sodium hydroxide followed by saturated aqueous sodium bicarbonate and the solvent removed below 40° under reduced pressure. Ethanol (30 ml) was twice added and removed. The residue was taken up in ethanol (3×20 ml), filtered and concentrated. Flash column chromatography eluting with 20% methanol/methylene chloride gave the title compound (700 mg) as a mixture of epimers.

$\tau$(D$_2$O) 2.14, 2.27 (1H,d,H-6) 4.10, 4.13 (1H,d,H-5), 5.00, 5.10(1H,m,H-1').

INTERMEDIATE 10

($\pm$)-Chloro-[1,2,3,4-tetrahydro-1-[(3$\beta$,4$\alpha$)-3-hydroxy-4-(hydroxymethyl)cyclopentyl]-2,4-dioxo-5-pyrimidinyl]mercury To Intermediate 9 (400 mg) in water (1.5 ml) was added mercuric acetate (595 mg) in water (4.5 ml) and the solution stirred at 50° for 4 h. Sodium chloride (256 mg) in water (1 ml) was added at 40° and the reaction mixture cooled (ice bath). Filtration of the solid, followed by drying at 60° in vacuo, afforded the title compound as a white solid which was used directly in the next stage.

INTERMEDIATE 11

(±)-(E)-Ethyl-3-[1,2,3,4-tetrahydro-1-[(3β,4α)-3-hydroxy-4-(hydroxymethyl)cyclopentyl]-2,4-dioxo-5-pyrimidinyl]-2-propenoate Intermediate 10 (390 mg), ethyl acrylate (0.75 ml) and dilithium palladium tetrachloride (0.1M solution in methanol, 8.7 ml) were stirred for 16 h under nitrogen. The reaction mixture was filtered, the precipitate washed with warm methanol (20 ml), and hydrogen sulphide gas bubbled through the combined methanol filtrate and washings to precipitate mercuric sulphide. The resulting mixture was filtered through Hyflo and the solvent removed in vacuo. Water (5 ml) was added, and then removed in vacuo at 30°. The residue was purified by flash chromatography eluting with chloroform-ethanol (6:1) to give the title compound (195 mg). $\tau([^2H_6]$ DMSO)(Mixture of epimers) 1.56, 1.70(1H,s,H-6), 2.54, 2.61(1H,d,C$\underline{H}$=CHCO$_2$Et), 3.08, 3.14(1H,d,=C$\underline{H}$CO$_2$Et).

INTERMEDIATE 12

(±)-(E)-3-[1,2,3,4-Tetrahydro-1-[(3β,4α)-3-hydroxy-4-(hydroxymethyl)cyclopentyl]-2,4-dioxo-5-pyrimidinyl]-2-propenoic acid Intermediate 11 (180 mg) in 0.5N aqueous sodium hydroxide (2.5 ml) was stirred at room temperature for 4 h. Dowex 50G-X8 cation exchange resin was added until the solution had pH4. The resin was filtered off and the filtrate evaporated in vacuo at 30°-35° to give the title compound as an off-white solid (131 mg); $\tau([^2H_6]$DMSO)(mixture of epimers) 1.70, 186(1H,s,H-6), 2.80, 2.86(1H,d,C$\underline{H}$=CHCO$_2$H), 3.23, 3.34 (1H,d, =C$\underline{H}$CO$_2$H).

INTERMEDIATE 13

(1α,3β,5α)-(±)-3-[[(1,1-Dimethylethyl)dimethylsilyl]oxy]-6-oxabicyclo[3,1,0]hexane A solution of (1α,3β,5α)-(±)-3-hydroxy-6-oxabicyclo[3,1,0]hexane (2.5 g) in dry DMF (25 ml) was treated with imidazole (3.40 g), the solution cooled to 0° under N$_2$ and t-butyldimethylsilyl chloride (4.15 g) added. The solution was stirred at 0° for 10 minutes, allowed to warm up to room temperature and stirring continued for a further 18 hours. The mixture was poured into water (150 ml) and extracted with pentane (2×150 ml). The organic phase was washed with water (2×150 ml), dried and concentrated to afford the crude product as a colourless oil. The latter was purified by flash chromatography, elution with 7% EtOAc/hexane affording the title compound as a colourless mobile oil (3.9 g); $\tau$(CDCl$_3$) 5.56 (1H, ABX, CHOSi), 6.52 (2H,s,

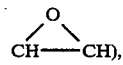

7.86-8.08 (4H, ABX, CH$_2$), 9.1 (9H,s, CMe$_3$), 9.96 (6H,s,Me).

INTERMEDIATE 14

(1α,2β,4α),-(±)-4-[[(1,1-Dimethylethyl)dimethylsilyl]oxy]-2-ethenylcyclopentanol A stirred suspension of cuprous iodide (190 mg) in dry THF (10 ml) at −30° under N$_2$ was treated dropwise with a solution of vinylmagnesium bromide (1M in THF, 10 ml) causing a greyish coloured suspension to form. The latter was stirred at −30° for 15 minutes and then a solution of Intermediate 13 (1.50 g) in dry THF (5 ml) added dropwise. The resulting dark coloured solution was stirred at −30° for 15 minutes, the mixture allowed to slowly warm to 0° (ca. 0.5 h) and then stirred for a further 2 hours. The reaction was quenched by pouring into saturated NH$_4$Cl solution (100 ml) and extracted with ether (2×100 ml). The combined organic extracts were washed with further saturated NH$_4$Cl solution (100 ml), dried and concentrated to afford the crude product as a pale yellow oil. The latter was purified by flash chromatography, elution with 8% EtOAc/hexane yielding the title compound as a colourless oil (1.25 g).

Analysis Found: C, 64.54; H, 11.07%. C$_{13}$H$_{26}$O$_2$Si requires: C, 64.40; H, 10.81%.

INTERMEDIATE 15

(1α,2β,4β)-(±)-[[(1,1-Dimethylethyl)dimethylsilyl]oxy]-2-hydroxy]cyclopentanemethanol Oxygenated ozone was bubbled through a solution of Intermediate 14 (6.68 g) in dry methanol (100 ml) and dichloromethane (50 ml) cooled to −70° until a deep blue colouration appeared. Sodium borohydride (1.05 g) was then quickly added in one portion and stirring at −70° continued for 30 minutes. Further sodium borohydride (1.05 g) was then added, the mixture allowed to slowly warm to room temperature (ca. 1 hr.) and then stirred for a further 30 minutes. The solvents were evaporated and the residue partitioned between dichloromethane (250 ml) and saturated ammonium chloride solution (250 ml). The aqueous layer was further extracted with dichloromethane 1×250 ml), the combined organics dried and concentrated to afford the crude product as an opaque viscous oil. The latter was purified by flash chromatography, elution with 5% MeOH/CH$_2$Cl$_2$ yielding the title compound as a viscous colourless oil (5.34 g.)

Analysis Found: C, 52.94; H, 10.89%. C$_{12}$H$_{26}$O$_3$Si.0.1H$_2$O requires: C, 58.06; H, 10.64%.

INTERMEDIATE 16

(1α,3β,4α)-(±)-(1,1-Dimethylethyl)dimethyl[[4-(methoxymethoxy)-3-[(methoxymethoxy)methyl]cyclopentyl]oxy]silane To a solution of Intermediate 15 (5.0 g), and N,N-diisopropylethylamine (7.87 g, 10.6 ml) in dry dichloromethane (100 ml), cooled to 0° under nitrogen, was added chloromethylmethyl ether (90%: 5.44 g, 5.19 ml,) dropwise over 10 minutes. The mixture was stirred at 0° for 5 minutes, allowed to warm up to room temperature and stirring continued overnight. The solution was washed with water (100 ml), the aqueous layer extracted with further dichloromethane (1×50 ml) and the combined organic layers dried. Concentration afforded the crude product as an orange oil which was purified by flash chromatography, elution with 10% EtOAc/hexane yielding the title compound as a colourless mobile oil (5.1 g)

Analysis Found: C, 57.51; H, 10.75%. C$_{16}$H$_{34}$O$_5$Si requires: C, 57.44; H, 10.55%.

INTERMEDIATE 17

(1α,3α,4β)-(±)-3-(Methoxymethoxy)-4-[(methoxymethoxy)methyl]cyclopentanol

A solution of Intermediate 16 (5.0 g) in THF (150 ml), stirred and cooled to 0°, was treated with tetra-n-butylammonium fluoride (1M in THF, 16 ml). The solution was allowed to warm up to room temperature and stirred for a further 4 hours. The mixture was concentrated to ca. 30 ml and subjected to flash chromatography. Elution with EtOAc/hexane (9:1) afforded the title compound as a pale yellow oil (3.2 g).

τ(CDCl₃)5.24–5.4 (4H,2$_x$AB, OCH₂O), 5.67 (1H,m,CHOCH₂), 5.9 (1H,m,CHOH), 6.4–6.7(8H,m+2s, OMe, CH₂O), 7.45(1H,m,CHCH₂O) 7.6 (1H,d,OH), 7.9–8.4(4H,m,2xCH₂)

INTERMEDIATE 18

(1α,3α,4β)-(±)-3-(Methoxymethoxy)-4-[(methoxymethoxy)methyl]cyclopentanol, 4-methylbenzenesulphonate A mixture of Intermediate 17 (1 g), paratoluenesulphonyl chloride (0.96 g) and dry pyridine (20 ml) was stirred at room temperature overnight. The pyridine was removed in vacuo at 35°, the residue taken up in dichloromethane (50 ml) and the solution washed with copper (II) sulphate solution (3×50 ml). The organic phase was dried and concentrated to afford the crude product as a yellow oil. The latter was purified by flash chromatography. Elution with EtOAc/hexane (1:1) afforded the title compound as a colourless oil (1.18 g)

Analysis Found: C, 54.68; H, 6.57%. C₁₇H₂₆O₇S requires: C, 54.52; H, 6.99%.

INTERMEDIATE 19

(1α,3β,4α)-(±)-1-[3-(Methoxymethoxy)-4-[(methoxymethoxy)methyl]cyclopentyl]-2,4(1H,3H)-pyrimidinedione A mixture of Intermediate 18 (374 mg), finely ground anhydrous potassium carbonate (414 mg) and uracil (336 mg) in dry DMSO (5 ml) was stirred under nitrogen at 90° for 15 hours. The resulting dark coloured solution was poured into brine (ca. 50 ml) and the mixture extracted with dichloromethane (3×30 ml). The organic phase was washed with brine (1×50 ml), dried and concentrated to afford the crude product as a yellow oil. The latter was purified by flash chromatography. Elution with 5–8% MeOH/CH₂Cl₂ afforded the title compound as a pale yellow oil (138 mg).

τ(CDCl₃) 1.13 (1H, br s, NH), 2.68 (1H, d, N—CH=CH), 4.25 (1H,d, N—CH=CH), 4.88 (1H, quin., H-1′), 5.35 (4H, s, OCH₂O), 5.88 (1H, dt, CH—O—CH₂ 5.3–5.46 (2H, m, CH₂O), 6.62 (6H, s, OMe).

INTERMEDIATE 20

(1α,3β,4α)-(±)-1-[3-Hydroxy-4-(hydroxymethyl)cyclopentyl]-2,4(1H,3H)-pyrimidinedione A mixture of Intermediate 19 and p-toluenesulphonic acid (1.40 g) in methanol (100 ml), was heated under gentle reflux on a steam bath for 1 hour. The solution was cooled, stirred and treated with R8050 polyvinylpyridine resin (Reilly Corporation) until pH6 was attained (ca. 2 g resin). Filtration and concentration yielded the crude product as a pale yellow oil. The latter was purified by flash chromatography. Elution with 15% MeOH/CH₂Cl₂ afforded the title compound as a white crystalline powder (1.1 g) m.p. 159°–162°.

EXAMPLE 1

(±)-(E)-5-(2-Bromoethenyl)-1-[(1α,3β,4α)-3-hydroxy-4-(hydroxymethyl)-cyclopentyl]-2,4-(1H,3H)-pyrimidinedione Intermediate 12 (110 mg) and potassium acetate (77 mg) in water (5 ml) was heated to 60°. N-bromosuccinimide (69.5 mg) was added in small portions over 5 min and the clear solution stirred at 60° for 10 min and then at room temperature for 2 h. The solvent was removed and the residue purified by column chromatography, eluting with chloroformethanol (9:1), to give the title compound (10 mg); τ(CD₃OD) 2.24(1H,s,H-6), 2.66(1H,d,CH=CHBr), 3.19(1H,d,CH=CHBr, 4.93(1H,m,H-1′), 5.81(1H,m,H-3′), 6.2–6.4(2H,m,H-5′,5″).

EXAMPLE 2

(±)-(E)-5-(2-Bromoethenyl)-1-[(1α,3β,4α)-3-hydroxy-4-(hydroxymethyl)-cyclopentyl]-2,4-(1H,3H)-pyrimidinedione A mixture of Intermediate 18 (374 mg), (E)-5-(2-bromovinyl)uracil (326 mg) and finely ground anhydrous potassium carbonate (207 mg) was stirred in dry DMSO (5 ml) at 90° under nitrogen for 4 h. The dark coloured mixture was poured into water (50 ml) and extracted with dichloromethane (3×25 ml). The combined organic phases were washed with brine (50 ml), dried and concentrated to afford a yellow oil. The latter was purified by flash chromatography eluting with 2% methanol/dichloromethane to give crude (±)-(E)-5-(2-bromoethenyl)-1-[(1α,3β,4α)-3-methoxymethoxy-4-[(methoxymethoxy)methyl]cyclopentyl]-2,4(1H,3H)-pyrimidinedione (42 mg) which was taken up in methanol (5 ml), para-toluenesulphonic acid (50 mg) was added and the solution refluxed for 1 h. The mixture was neutralised by the addition of R8050 polyvinylpyridine resin (Reilly Corporation) and subsequently evaporated onto flash silica (ca 1 g). The latter was applied to a flash chromatography column eluting with 10% methanol/dichloromethane to yield the title compound (11 mg). m.p. 179°–183° (d).

EXAMPLES OF PHARMACEUTICAL FORMULATIONS

EXAMPLE A

| Oral Capsule | |
| --- | --- |
| | per capsule |
| Product of Example 1 or 2 | 125.0 mg |
| Sodium starch glycollate (Explotab) | 12.5 mg |
| Microcrystalline cellulose (Avicel PH) | 110.0 mg |
| Magnesium stearate | 2.5 mg |
| Capsule fill weight | 250.0 mg |

Make a pre-blend of the magnesium stearate, sodium starch glycollate and a portion of the active compound and pass through a 250 μm screen. Then blend with the microcrystalline cellulose and the remaining active compound. Fill the blend into two-piece hard gelatin capsule shells to a target fill weight of 250 mg per capsule.

EXAMPLE B

Topical Cream

| | Quantities for 1 kg |
|---|---|
| Product of Example 1 or 2 | 20 g |
| Chlorocresol | 1.0 g |
| Cetostearyl alcohol | 72 g |
| White soft paraffin | 150 g |
| Liquid paraffin | 60 g |
| Cetomacrogol 1000 | 18 g |
| Disodium hydrogen phosphate | 2.0 g |
| Sodium dihydrogen phosphate (dihydrate) | 1.0 g |
| Sodium hydroxide or phosphoric acid to pH | 7.0 |
| Distilled water to | 1.00 kg |

Heat 650 ml water and dissolve the chlorocresol and phosphates. Take 100 ml of the solution, dissolve 2.5 g cetomacrogol 1000 and cool. Disperse the milled drug in the solution using a high shear mixer. Melt the cetostearyl alcohol, white soft paraffin, liquid paraffin and the remainder of the cetomacrogol 1000 together and mix with the remainder of the aqueous phase at not more than 65° C. Stir until cool. Add the drug slurry to the aqueous cream base with stirring. Check the pH and adjust to pH 7.0 with a solution of phosphoric acid or sodium hydroxide as appropriate. Make up to volume with water and stir. Fill into lacquered aluminium tubes at a fill weight of 30 g and seal.

EXAMPLE C

Eye Ointment

| | Quantities for 1 kg |
|---|---|
| Product of Example 1 or 2 | 30 g |
| White soft paraffin | 770 g |
| Liquid paraffin | 200 g |

Strain the paraffins and sterilise by heating at 150° C. for 1 hour and cool. Disperse the sterile milled drug aseptically in the liquid paraffin. To the molten white soft paraffin add the drug slurry and stir until set. When cool, fill into sterile tin eye ointment tubes at a fill weight of 3.0 g and seal.

We claim:

1. Compounds of formula (I):

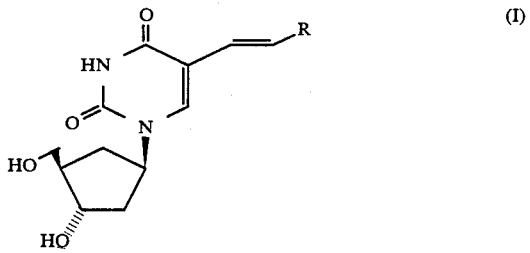

wherein R is a chlorine, bromine or iodine atom and physiologically acceptable salts thereof with bases.

2. E-5-(2-bromoethenyl)-1-[(1α,3β,4α)-3-hydroxy-4-(hydroxymethyl)cyclopentyl]-2,4(1H,3H)-pyrimidinedione.

3. Compounds as claimed in claim 1 in (+) or (−) isomeric form.

4. Compounds as claimed in claim 1 having a 1R,3S, 4R configuration in the cyclopentane ring.

5. Pharmaceutical compositions comprising, as an active ingredient, an antivirally effective amount of at least one compound as defined in claim 1 in association with a physiologically acceptable carrier or excipient.

6. A method of treating a patient infected with or susceptible to infection by a virus which comprises administering to said patient an effective amount of a compound as claimed in claim 1.

* * * * *